United States Patent [19]

Spietschka et al.

[11] Patent Number: 4,614,803
[45] Date of Patent: Sep. 30, 1986

[54] PROCESS FOR THE PREPARATION OF DRY ALKALI METAL SALTS OF 1,8-NAPHTHALIMIDE

[75] Inventors: Ernst Spietschka, Idstein/Taunus; Manfred Urban, Wiesbaden, both of Fed. Rep. of Germany

[73] Assignee: Hoechst Aktiengesellschaft, Fed. Rep. of Germany

[21] Appl. No.: 738,577

[22] Filed: May 28, 1985

[30] Foreign Application Priority Data

May 30, 1984 [DE] Fed. Rep. of Germany ....... 3420161

[51] Int. Cl.$^4$ ............................................. C07D 221/04
[52] U.S. Cl. ....................................................... 546/98
[58] Field of Search ........................................... 546/98

[56] References Cited

U.S. PATENT DOCUMENTS 3,997,572 12/1976 Cusic et al. ............................ 546/98
4,051,246 9/1977 Wade et al. ............................ 546/98

FOREIGN PATENT DOCUMENTS 2137242 2/1973 Fed. Rep. of Germany ........ 546/98

OTHER PUBLICATIONS

Karishin et al., Zh.Obschchey Khimii, vol. 29, 1959, pp. 3048–3050.
Fieser et al., Lehrbuch der Ogranischen Chemie, Verlag Chemie, Weinheim/Bergstr., 1954, p. 251.
Beyer, Lehrbuch der Organischen Chemie, S. Hirzel Verlag, Leipzig, 1968, p. 208.
Meisenheimer, *Berichte Deutsch. Chem. Ges.* 37, p. 4315 (1904).

*Primary Examiner*—Henry R. Jiles
*Assistant Examiner*—J. Richter
*Attorney, Agent, or Firm*—Connolly and Hutz

[57] ABSTRACT

Process for the preparation of dry alkali metal salts of 1,8-naphthalimide, which comprises allowing concentrated alkali metal hydroxide solutions to run into solid 1,8-naphthalimide in a molar ratio, at a rate corresponding to the degree of reaction, with vigorous stirring in vacuo at an elevated internal temperature, and then carrying out drying without intermediate isolation of the alkali metal salt formed.

7 Claims, No Drawings

PROCESS FOR THE PREPARATION OF DRY ALKALI METAL SALTS OF 1,8-NAPHTHALIMIDE

The present invention relates to an improved, industrially simple process for the preparation of dry alkali metal salts of 1,8-naphthalimide with a high space/time yield.

The dry alkali metal salts of 1,8-naphthalimide are industrially useful intermediate for the preparation of perylene-3,4,9,10-tetracarboxylic acid diimide (West German laid open Patent Application No. 3,314,430). The alkali metal salts of 1,8-naphthalimide are known compounds, the following processes for the preparation of which are described in the literature:

According to the process described in U.S. Pat. No. 4,051,246, the sodium salt of 1,8-naphthalimide is obtained in an organic solvent by reacting 1,8-naphthalimide with a methanolic sodium hydroxide solution, and is isolated from the solution by filtration with suction and then dried. The isolation from the solvent and the regeneration of the solvent are industrially expensive process steps. The journal Z. obs. Chim. 29 (1959) No. 95, pages 3048–3050 reports that the alkali metal salts of 1,8-naphthalimide can be obtained by reacting 1,8-naphthalimide with alkalis in aqueous solution. In this process, the end products must be isolated from the aqueous suspension by filtration and then dried and the effluent obtained must be treated. U.S. Pat. No. 3,997,572 describes the preparation of the potassium salt of 1,8-naphthalimide by reacting 1,8-naphthalimide with potassium hydroxide in methanolic solution, the methanol subsequently being removed by distillation in vacuo. This process is carried out in high dilution in an organic solvent, which must be removed by expensive distillation.

It has now been found that dry alkali metal salts of 1,8-naphthalimide can be prepared in an industrially extremely simple manner by allowing concentrated alkali metal hydroxide solutions, such as, for example, concentrated sodium hydroxide solution or potassium hydroxide solution, to run into solid 1,8-naphthalimide in a molar ratio, i.e. in a molar ratio of 1:1, with vigorous stirring in vacuo, advantageously under about 20–200 mm Hg, and at an elevated internal temperature, advantageously at temperatures of about 60°–100° C. (drying kettle conditions) at a rate corresponding to the degree of reaction, i.e. in portions, for example by dropwise addition and avoiding a relatively large local excess of alkali metal hydroxide solution at the inlet point, complete reaction, i.e. complete formation of the alkali metal salts of 1,8-naphthalimide, being achieved, and then carrying out drying without intermediate isolation of the alkali metal salts formed.

The water originating from the concentrated alkali metal hydroxide solution employed and the water of reaction formed by reaction of the 1,8-naphthalimide with the alkali metal hydroxide solution (water of neutralization) can be removed by being distilled over during or after completion of the addition of the alkali metal hydroxide solution. Instead of dry 1,8-naphthalimide, it is also possible to employ 1,8-naphthalimide with a small water content, such as is prepared by the process described in German Pat. No. 2,137,242.

It is to be considered surprising that the reaction of the 1,8-naphthalimide in solid form with concentrated alkali metal hydroxide solutions, i.e. in the presence of only very small amounts of water, leads to a complete reaction, since the known processes must always be carried out in solution with dilute alkalis. In view of the fact that carboxylic acid imides or carboxylic acid amides are hydrolyzed under the influence of strong alkalis at elevated temperature, it was not to be expected that the desired reaction would succeed to the actual extent (achievement of quantitative yield without hydrolysis) (FIESER Lehrbuch der organischen Chemie (Textbook of Organic Chemistry) 1954, page 251; BAYER, Lehrbuch der organischen Chemie (Textbook of Organic Chemistry) 1963, page 208).

EXAMPLE 1

197 g of 1,8-naphthalimide are taken in a 1 l V4A stainless steel autoclave and heated to 95° C., a vacuum of 100 mm Hg being applied. 111 g of 48% strength potassium hydroxide solution are then added dropwise under the temperature and pressure conditions mentioned in the course of 5 hours, with stirring, after which the mixture is subsequently stirred for a further 6 hours (until no further water passes over). The autoclave is then emptied.

232 g of potassium 1,8-naphthalimide are obtained, corresponding to a yield of 98.7% of theory.

EXAMPLE 2

197 g of 1,8-naphthalimide are taken in a 1 l V4A stainless steel autoclave and heated to 95° C., a vacuum of 100 mm Hg being applied. 121 g of 33% strength sodium hydroxide solution are then added dropwise under these temperature and pressure conditions in the course of 5 hours, with stirring, after which the mixture is subsequently stirred for a further 6 hours (until no further water passed over). The autoclave is then emptied.

219 g of sodium 1,8-naphthalimide are obtained, corresponding to a yield of 100% of theory.

We claim:

1. A process for the preparation of a dry alkali metal salt of 1,8-naphthalimide, which comprises allowing a concentrated alkali metal hydroxide solution to run into solid 1,8-naphthalimide in a molar ratio at a rate corresponding to the degree of reaction, with vigorous stirring in vacuo at an elevated internal temperature, and then carrying out drying without intermediate isolation of the alkali metal salt formed.

2. The process as claimed in claim 1, wherein the reaction is carried out at temperatures of 60°–100° C.

3. The process as claimed in claim 1, wherein the reaction is carried out under a pressure of 20–200 mm Hg.

4. The process as claimed in claim 1, wherein concentrated sodium hydroxide solution or potassium hydroxide solution is allowed to run in.

5. The process as claimed in claim 1, wherein dry 1,8-naphthalimide is employed.

6. The process as claimed in claim 1, wherein the solid 1,8-naphthalimide employed contains a small amount of water.

7. The process as claimed in claim 1, wherein water originating from the concentrated alkali metal hydroxide solution employed and the water of reaction formed are removed by distillation during or after the reaction.

* * * * *